United States Patent [19]

Meserol et al.

[11] Patent Number: 4,873,993

[45] Date of Patent: Oct. 17, 1989

[54] CUVETTE

[75] Inventors: Peter M. Meserol, Montville; Thomas Palmieri, Paramus, both of N.J.

[73] Assignee: Personal Diagnostics, Inc., Whippany, N.J.

[21] Appl. No.: 69,505

[22] Filed: Jul. 13, 1987

Related U.S. Application Data

[63] Continuation-in-part of Ser. No. 888,752, Jul. 22, 1986, abandoned.

[51] Int. Cl.[4] .................................................. A61B 5/00
[52] U.S. Cl. .................................... 128/760; 356/246; 356/39; 128/763; 128/770
[58] Field of Search ............... 128/760, 762, 763, 770, 128/633; 422/102; 356/244, 246, 39–42

[56] References Cited

U.S. PATENT DOCUMENTS

| | | | | |
|---|---|---|---|---|
| 3,123,066 | 3/1964 | Brumley | .................. | 356/41 |
| 3,847,482 | 11/1974 | Sokol et al. | .................. | 356/40 |
| 4,176,451 | 12/1979 | McMorrow | .................. | 128/768 |
| 4,303,336 | 12/1981 | Cullis | .................. | 356/39 |
| 4,648,408 | 3/1987 | Hutcheson et al. | .................. | 128/770 |

FOREIGN PATENT DOCUMENTS 947908  1/1964  United Kingdom ................ 128/770

Primary Examiner—Max Hindenburg
Assistant Examiner—J. P. Lacyk
Attorney, Agent, or Firm—R. Gale Rhodes, Jr.

[57] ABSTRACT

Cuvette with or without a lancet secured thereto and extending therefrom for producing skin puncture to produce body fluid of interest, the cuvette is made of optically transparent material and is provided with a shape and a plurality of optical elements such as integrally formed optical elements for causing a light beam to pass therethrough by total internal reflectance and for causing the beam of light to be reflected back along a line different from the direction of the line of entry of the beam of light into the cuvette such as back along a line generally parallel to the line of entry of the beam of light into the cuvette and in the opposite direction to the direction of entry of the beam of light into the cuvette.

5 Claims, 6 Drawing Sheets

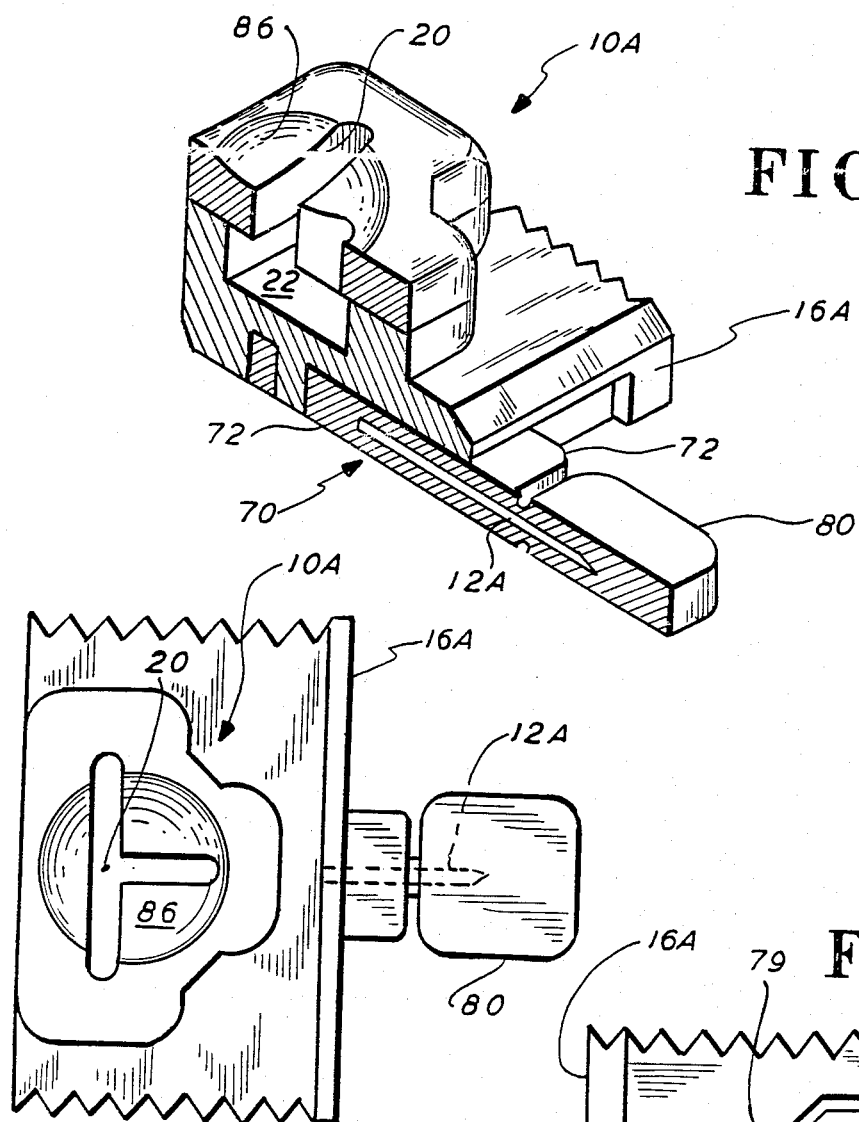
FIG. 10
FIG. 11
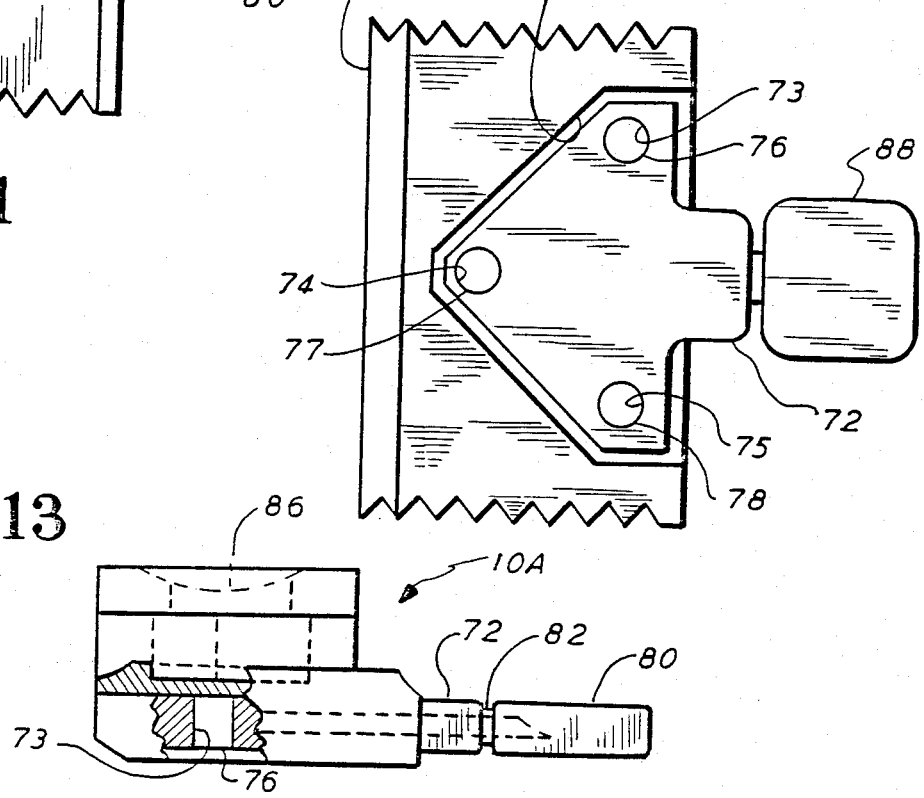
FIG. 12
FIG. 13

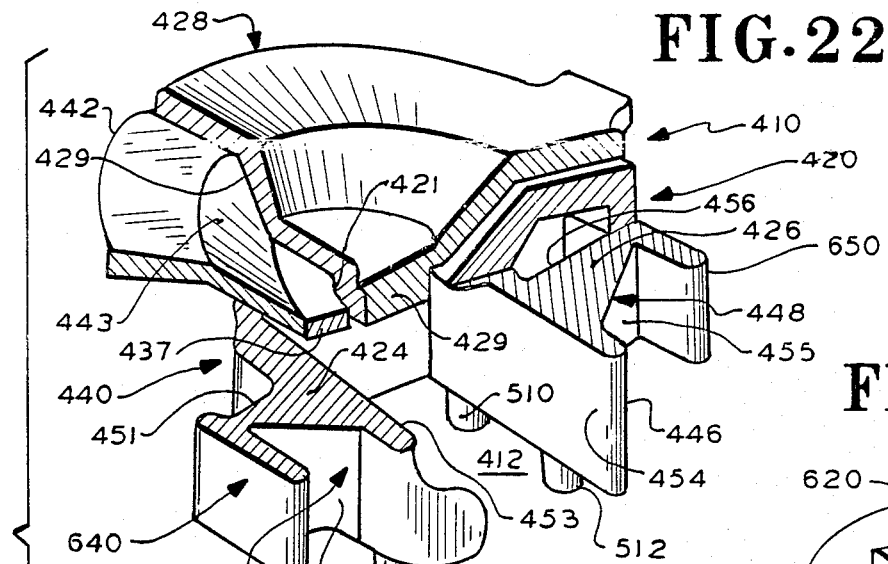
FIG. 22
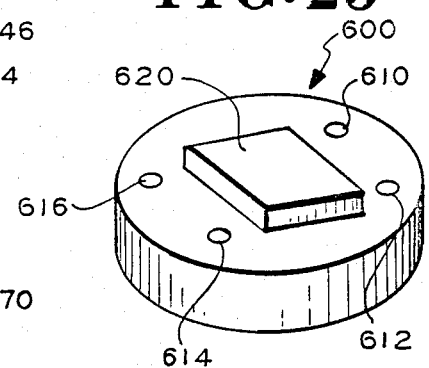
FIG. 25
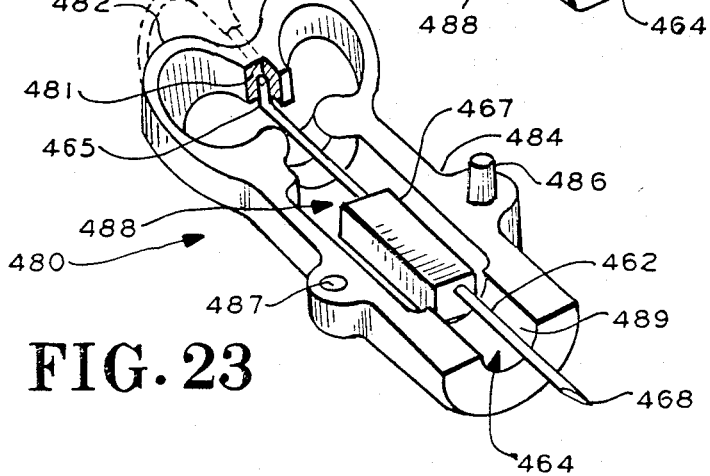
FIG. 23
FIG. 24

CUVETTE

CROSS-REFERENCE TO RELATED APPLICATIONS

This application is a continuation-in-part application of patent application Ser. No. 888,752 filed July 22, 1986 now abandoned entitled IMPROVED CUVETTE, Peter M. Meserol and Thomas Palmieri inventors, and assigned to the same assignee as the present application.

BACKGROUND OF THE INVENTION

This invention relates generally to a new and improved cuvette, relates particularly to a new and improved combination of cuvette and lancet, and still more particularly relates to a new and improved cuvette of optically tranparent material of a shape and provided with optical elements such as integrally formed optical elements for causing a beam of light to pass therethrough by total internal reflectance and for causing the beam of light to be reflected back along a line different from the direction of the line of entry into the cuvette such as back along a line generally parallel to the line of entry of the beam of light into the cuvette and in the opposite direction of the direction of entry of the beam of light into the cuvette.

The prior art, as well known to those skilled therein, is replete with a multitude of different cuvettes of different sizes and shapes, of different materials, and for many different purposes. Included in such prior art cuvettes are cuvettes of optically transparent material for receiving an optically transparent medium including a reagent test system and which in the presence of an analyte reacts with the analyte to cause a change in at least one optical transmissive property or characteristic of the medium such as a change in color, turbidity, light absorption, etc.; typically, after the reaction, a beam of light (sometimes referred to in the art as an analytical light beam) transmitted through the medium is measured and compared with the measurement of a beam of light transmitted previously through the medium prior to the reaction, the light beams are compared and a determination of the analyte, or a characteristic thereof, made, e.g. determination of a substance found in body fluids such as the level of extra cellular (serum) glucose in blood.

While various prior art optically transmissive or transparent cuvettes function well for their intended purpose, there exists a need for a new and improved optically transparent or transmissive cuvette for causing a light beam to pass therethrough, and through a medium contained therein and undergoing (or having undergone) a change in optical transmissive characteristic, by total internal reflectance; total internal reflectance provides the light beam with a long path (as distinguished from the path of a light beam passing straight therethrough) providing averaging of the reaction occurring at different regions of the medium which in turn enhances analyte determination.

In addition, there exists a need for an optically transmissive transparent cuvette which causes the beam of light passing therethrough to be reflected back along a line generally parallel to the line of entry of the beam of light into the cuvette and in the opposite direction of the entry of the beam of light into the cuvette. This parallel reversal in direction permits the light beam source and light beam detector to be mounted parallel and directed in the same direction towards the cuvette which is desirable in many applications such as, for example, the one taught in U.S. patent application Ser. No. 888,754, entitled OPTICAL ANALYZER, filed July 22, 1986, Peter M. Meserol et al. inventors, and assigned to the same assignee as the present invention.

As noted by way of example above, a body fluid such as blood, or a sample portion thereof, is often the analyte of interest to be reacted with a reagent system in the cuvette to perform analyte determination such as the determination of the amount of blood extra cellular (serum) glucose present in the blood. Such blood is typically produced by puncturing the skin of a person. In the prior art, the lancet and cuvette are typically physically separate objects thereby making it somewhat tedious or at least difficult to first puncture the human skin with a lancet, dispose of the lancet, and thereafter transfer the blood to a test object such as a bibulous test strip. Accordingly, there exists a need in the art for the combination of a cuvette and lancet to facilitate skin puncture with resulting production of a body fluid of interest such as blood for ready transfer to a physically associated cuvette for analysis or determination of the body fluid.

SUMMARY OF THE INVENTION

Cuvette with or without a lancet secured thereto and extending therefrom for producing skin puncture to produce body fluid of interest, the cuvette is made of optically transparent material and is provided with a shape and optical elements such as integrally formed optical elements for causing a light beam to pass therethrough by total internal reflectance and for causing the beam of light to be reflected back along a line different from the direction of the line of entry of the beam of light into the cuvette such as back along a line generally parallel to the line of entry of the beam of light into the cuvette and in the opposite direction to the direction of entry of the beam of light into the cuvette.

DESCRIPTION OF THE DRAWINGS

FIG. 10 is a perspective view, in vertical cross-section, taken generally along the line 10—10 in FIG. 9 and in the direction of the arrows;

FIG. 11 is a plan view of the top of the alternate invention embodiment of FIG. 9;

FIG. 12 is a plan view of the bottom of FIG. 9;

FIG. 13 is a side elevational view, partially in cross-section, of the invention embodiment of FIG. 9;

FIG. 22 is an exploded assembly view, with the structure shown therein being shown in perspective and partially in cross-section, of a further alternate embodiment of the combination cuvette and lancet of the present invention;

FIG. 23 is a perspective view of the bottom member of the lancet support member of the present invention illustrating the advancement of the lancet to produce a skin puncture to provide a body fluid of interest;

FIG. 24 is a view, in partial cross-section, of a protective member or shroud for the lancet tip; and FIG. 25 is a view, in perspective, of alternate structure for closing the bottom of the cavity of the cuvette of FIGS. 17–22.

DETAILED DESCRIPTION

Figure 1:
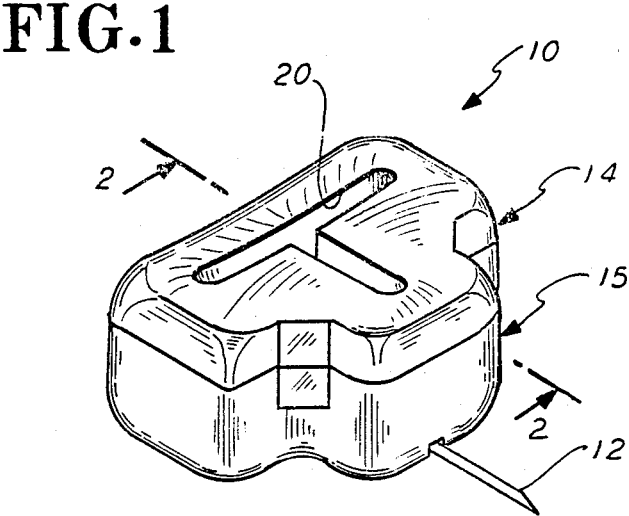
FIG. 1 is a perspective view of a combination cuvette and lancet embodying the present invention.
Figure 2:
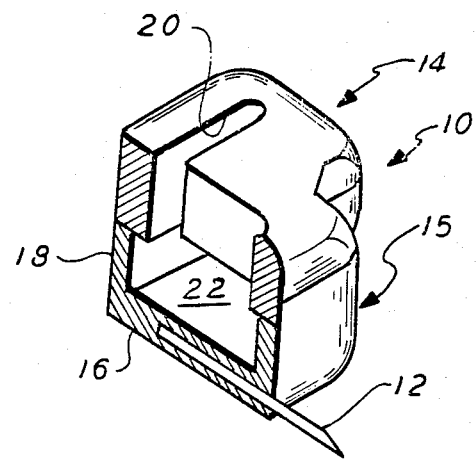
FIG. 2 is a vertical cross-sectional view, in perspective, taken generally along the line 2—2 in FIG. 1 in the direction of the arrows.
Figure 3:
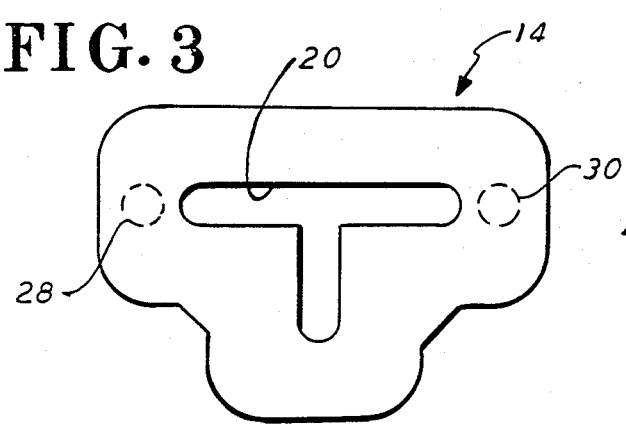
FIG. 3 is a plan view of a T-shaped cuvette top of an embodiment of the present invention.
Figure 4:
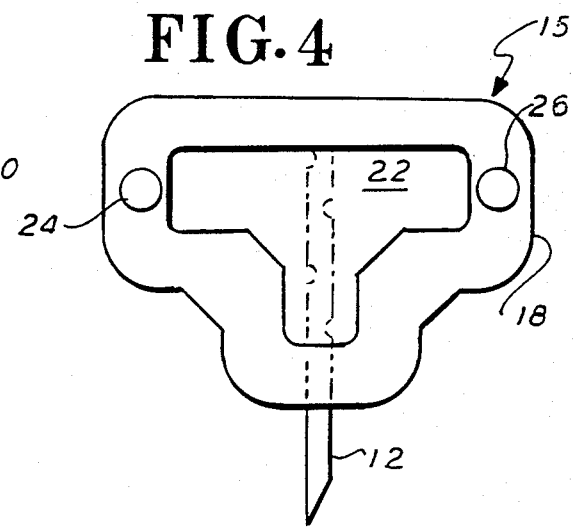
FIG. 4 is a plan view of a T-shaped cuvette bottom of an embodiment of the present invention.

Referring now to FIGS. 1–4, there is illustrated a combination cuvette 10 and lancet 12 embodying the present invention. Cuvette 10 includes a top 14, and a bottom 15 including a base 16 and a closed wall 18 formed integrally with the base and extending upwardly therefrom. The top 14 is generally planar and as may be best een in FIG. 3 is generally T-shaped in plan and is provided with an access slot 20 extending therethrough and also generally T-shaped in plan. The bottom 15 and wall 18 are generally T-shaped in plan, FIG. 4, and cooperatively provide a cavity indicated by general numerical designation 22 which, as may be best seen in FIG. 4, is also of generally T-shape. As may be noted from FIGS. 1 and 2, the top and bottom are complementary in size and shape. The top of the closed wall 18, as may be noted from FIG. 4, is provided with a pair of upwardly extending tapered posts 24 and 26 for being received in interference engagement with a pair of inwardly extending tapered holes 28 and 30, FIG. 3, formed in the bottom of the top 14 to secure the top and bottom together. The lancet 12 may be secured to the cuvette bottom 15 by providing the rearward portion of the lancet with an irregular shape as shown in dashed outline in FIG. 4 and by molding the cuvette bottom 15 around the rearward portion of the lancet.

Referring again to FIGS. 1 and 2, and particularly to the access slot 20, it will be understood that the access slot is of a predetermined size smaller than the cavity 22 for metering a predetermined volume of a fluid of interest, such as blood, into the cavity upon a larger volume of the fluid being present at and or wiped across the access slot.

The cavity 22, FIGS. 2 and 4, may be filled with a medium such as the optically transparent gel body provided with a reagent test system as disclosed in U.S. patent application Ser. No. 888,755, filed on July 22, 1986, entitled GLUCOSE ASSAY, Rita C. Prodell et al. inventors, and assigned to the same assignee as the present invention. Upon reaction of a fluid of interest, such as a body fluid of interest (e.g. blood plasma) with the reagent test system, the medium undergoes a change in at least one optical transmissive property, as described above, permitting optical determinations of the fluid or analyte as described above.

Figure 5:
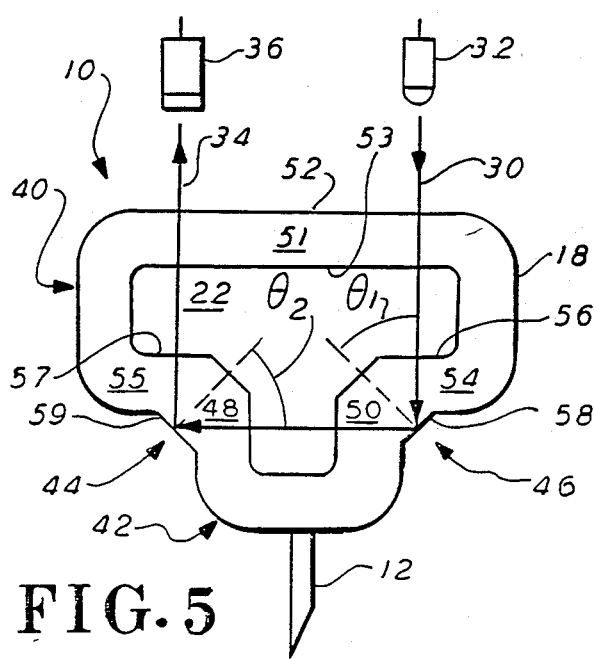
FIG. 5 is a diagrammatical illustration in plan of the optical path of a light beam provided by the cuvette of an embodiment of the present invention.

Referring now to FIG. 5, it will be generally understood that the cuvette 10 of the present invention, particularly closed wall 18, is provided with a shape and a plurality of integrally formed optical elements for causing a beam of light, such as light beam 30 from a suitable source such as photoemissive element 32, to pass through the cuvette and a medium received within the cavity 22, by total internal reflectance and to be reflected, as indicated by reflected light beam 34, back along a line generally parallel to the line of entry of the beam of light 30 into the cuvette and in the opposite direction of the entry of the beam of light into the cuvette. Such parallel reflectance, as noted above, permits the optical elements, e.g. photoemissive and photodetector elements 32 and 36, to be positioned parallel and opposite the same side or portion of the cuvette thereby permitting, for example, the lancet 12 to be secured to the cuvette on the opposite side of the optical elements 32 and 36 whereby the mechanical action of the cuvette, such as body skin piercing, does not interfere with the optical function, and particularly the optical elements such as 32 and 36 which may be associated with the cuvette as described above.

Figure 7:
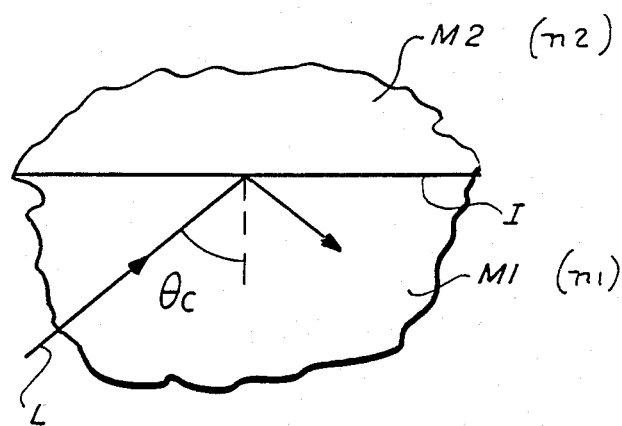
FIG. 7 is a diagrammatical illustration of the critical angle for total internal reflectance.

With regard to total internal reflectance, and as known to thoe skilled in the art and as illustrated in FIG. 7, the critical angle $\theta_c$ for total internal reflectance is given by the following:

$$\theta_c = \sin^{-1} n_{12}$$

where $n_{12}$ is the relative index of refraction at the interface I between the internal medium $M_1$ and the external medium $M_2$ and is less than unity; where $n_{12} = n_1/n_2$, and where $n_1$ is the index of refraction of the internal medium $M_1$ through which the beam of light L is transmitted obliquely, and where $n_2$ is the index of refraction of the external medium $M_2$ towards which the beam of light is being transmitted obliquely. Thus, upon the light beam L of FIG. 7 striking the interface I at or above (at an angle greter than) the critical angle $\theta_c$, the light beam is reflected back into the medium $M_1$, but upon the light beam L striking the interface I below (at an angle less than) the critical angle $\theta_c$, the light beam is refracted and passes further obliquely through medium $M_2$.

Figure 8:
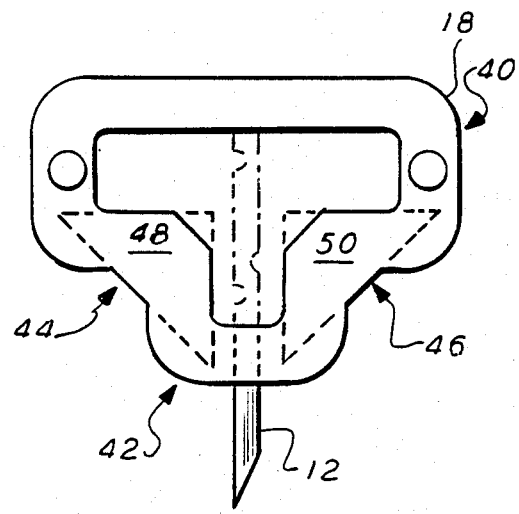
FIG. 8 is a view substantially the same as FIG. 5 but illustrating the presence of integrally formed optical elements in a cuvette wall embodying the present invention.

Referring again to FIG. 5, it will be generally understood that the generally T-shaped closed wall 18 includes a cross-bar portion indicated by general numerical designation 40 and a descender portion indicated by general numerical designation 42 and wherein the cross-bar portion 40 intersects the descender portion 42 at two generally right angle portions 44 and 46. It will be particularly noted and understood that two reflecting prisms, 48 and 50, are formed respectively, and integrally, at the right angle portions 44 and 46 of the closed wall 18. The presence or existence of such reflecting prisms 48 and 50 may be better understood by reference to FIG. 8 wherein the portions of typical reflecting prisms of the type known to the art but missing in FIG. 5 are shown in dashed outline in FIG. 8. Thus, by reference to FIG. 8, it will be appreciated that the dashed outline of the reflecting prisms 48 and 50, which are redundant to the present internal reflectance, are merely removed or are not present in the embodiment of FIG. 5.

It will be further noted and understood in greater detail, and referring again to FIG. 5, that the closed wall 18 includes a first portion 51 having parallel inner and outer surfaces 52 and 53 and a pair of opposed portions 54 and 55 having, respectively, inner surfaces 56 and 57 parallel to inner and outer surfaces 52 and 53 of the first portion 51 and, respectively, outer angular surfaces 58 and 59 disposed at a predetermined angle, e.g. approximately 45°, with respect to the parallel surfaces 52, 53, 56 and 57. Thus, it will be understood that in accordance with the teachings of the present invention cuvette 10, particularly closed wall 18, is provided with a shape and integrally formed reflecting prisms 48 and 50 to cause the beam of light 30 upon entry into the cuvette perpendicular to the inner and outer parallel surfaces 52 and 53 of the first portion 51 to pass through the first portion substantially without refractance, through the cavity 22 and a medium received therein, and through opposed portion 54 substantially without refractance and to internally strike the outer angular surface 58 of the opposed portion 54 at an angle $\theta_1$ above the critical angle $\theta_c$ (as described above) for total internal reflectance and to be reflected internally therefrom through the opposed portion 54 substantially without refractance, again through the cavity 22 and the medium contained therein and through the other opposed portion 55 substantially without refractance and to strike internally the outer angular surface 59 of the opposed portion 55 at an angle $\theta_2$ above the critical angle for total internal reflectance and to be reflected internally therefrom through the opposed portion 55, again through the cavity 22 and the medium contained therein and through the first portion 51 and to exit the cuvette 10 substantially without refractance and be reflected, as indicated by arrow 34, back along a line generally parallel to the line of entry of the beam of light into the cuvette, as indicated by arrow 30, and in the opposite direction thereto. It will be further understood that in the embodiment of FIG. 5 the medium received in the cavity 22 is less dense than the optically transparent material, e.g. a suitable polymeric material, of which the closed wall 18 is made and hence the relative index of refraction between the medium and the wall material is greater than unity and thus no critical angle for reflectance is possible at this interface, however, it will be further understood that the optically transparent material of which the closed wall 18 is made is more dense than the surrounding medium, such as air, and that the relative index of refraction between the wall material of which the closed wall 18 is made and the surrounding medium is less than unity and hence a critical angle $\theta_c$ for total internal reflectance is present or possible.

Figure 6:
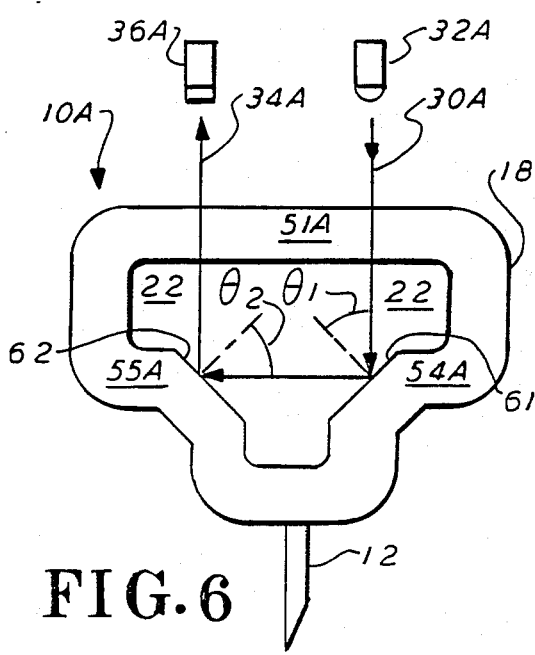
FIG. 6 is a diagrammatical illustration of an embodiment alternative to that illustrated in FIG. 5.

However, upon the optically transparent material of which the closed wall 18 is made being less dense than the medium contained in the container 22 but more dense than the surrounding medium such as air, the situation illustrated in FIG. 6, total internal reflectance will take place at the interface between the medium and the inner wall surface, particularly the inner angular surfaces 61 and 62 of the closed wall 18 disposed at substantially 45° with respect to the path of the beam of light. Otherwise, it will be understood that the embodiment of FIG. 6 functions in the same manner for total internal reflectance but at a different interface than the embodiment of FIG. 5.

Figure 9:
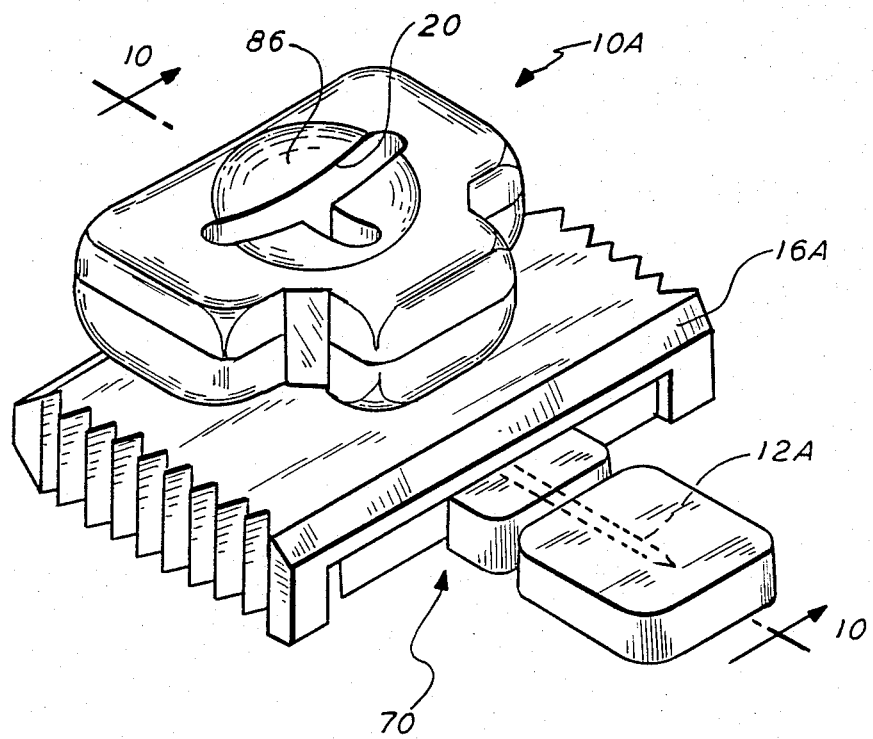
FIG. 9 is a perspective view of an alternate embodiment of a combination cuvette and lancet embodying the present invention.

A further alternate embodiment of the present invention is illustrated in FIG. 9 and includes a cuvette 10A which, it will be understood, is of the same or substantially the same structure as the embodiments described above and illustrated in FIGS. 2, 5 and 6, except that cuvette 10A is provided with a base 16A of the size and shape shown in FIGS. 9-13. In addition, embodiment 10A further includes a lancet support member indicated by general numerical designation 70 having a lancet 12A received wholly therein. Lancet support member 70 includes a first or rearward portion 72 provided with a plurality of tapered holes 73, 74 and 75, best seen in FIGS. 12 and 13, for receiving a plurality of tapered posts 76, 77 and 78 extending downwardly from the bottom of the base 16A in an interference fit whereby the lancet support member 70 is secured to the underside of the base 16A residing in a recess 79, FIG. 12, extending inwardly into the bottom of the base 16A. In addition, the lancet support member 70 includes an integrally formed forward portion 80 having the forward portion of the lancet 12A residing therein and wherein the forward and rearward portions of the lancet support member 70 are connected by an integrally formed intermediate portion 82 of reduced thickness to facilitate breaking of the forward portion away from the rearward portion to expose the forward portion of the lancet to puncture the skin, for example the skin of a human being, to produce a body fluid of interest.

Further, embodiment 10A, as may be best noted in FIG. 9, has a spherical depression 86 formed in the top of the cuvette 10A and coextensive with the access slot 20; depression 86 facilitates wiping of a fluid of interest across the access slot 20 and entry of the fluid into and through the access slot into the cavity 22 (FIG. 10) provided internally of the cuvette 10A.

Figure 14:
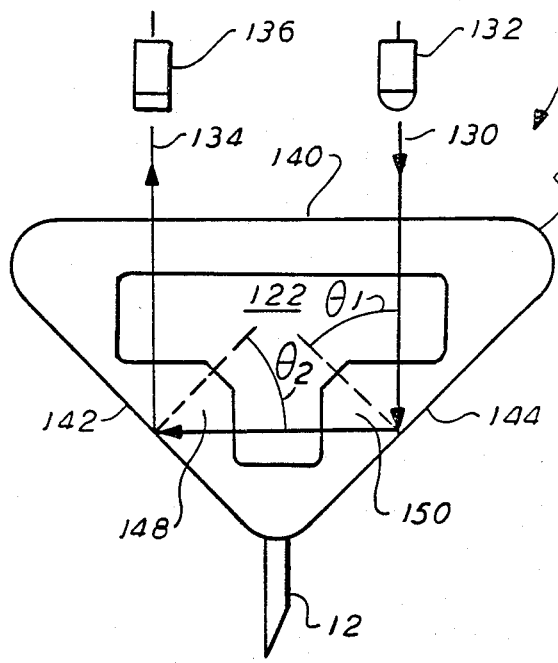
FIGS. 14, 15 and 16 are views similar to FIGS. 5 and 6 but of additional alternate embodiments of the present invention.
Figure 15:
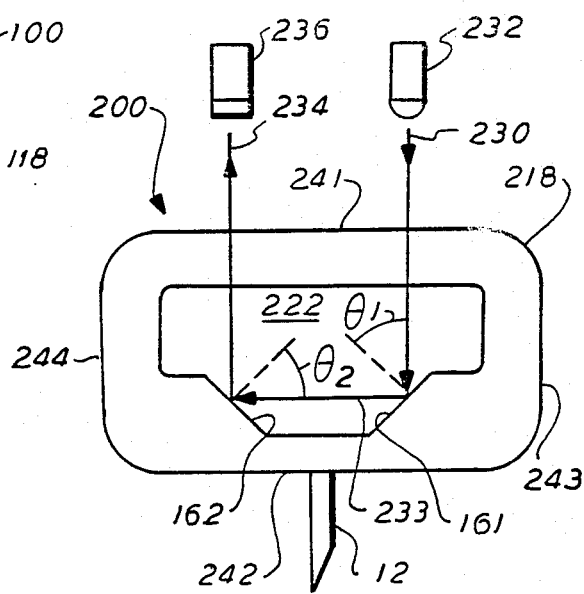
Figure 16:
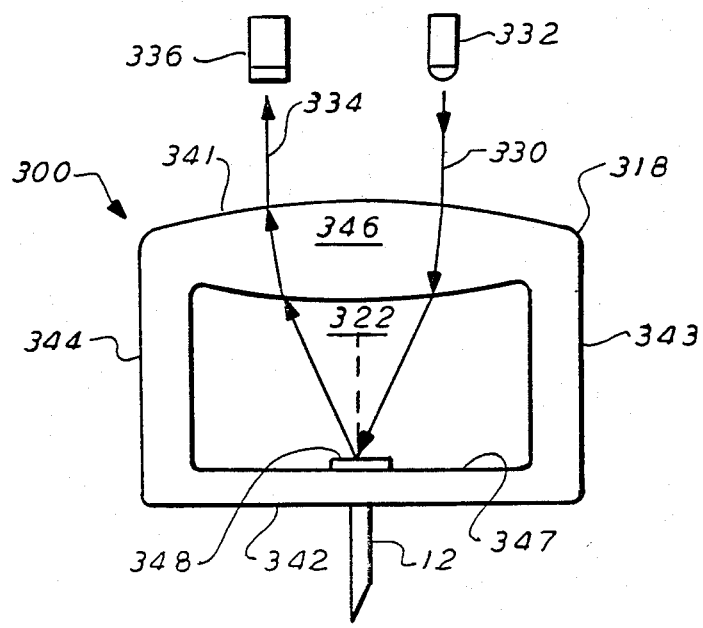
Figure 17:
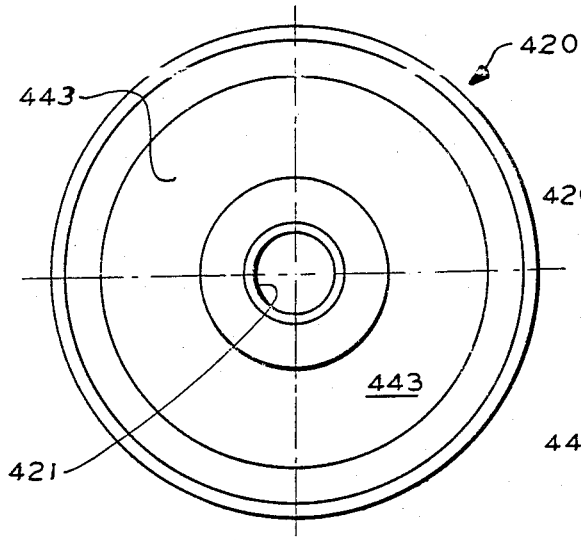
FIG. 17 is a plan view of the top of an alternate embodiment of a cuvette of the present invention.

Referring now to FIGS. 14, 15 and 16, there are illustrated additional alternate embodiments of the improved cuvette of the present invention identified, respectively, by general numerical designations 100, 200, and 300; these views are similar to views 5 and 6 described above.

Improved cuvette 100, FIG. 14, is generally triangularly-shaped and includes a closed wall 118 also generally triangularly-shaped which, it will be understood, overlies a generally triangularly-shaped base and in cooperation therewith provides the generally triangularly shaped cavity 122 for receiving the above-described optically transparent medium including a reagent test system for reacting with a sample portion of a body fluid of interest. The closed wall 118 includes a transverse portion 140 for being disposed generally perpendicular to a photoemitter 132 for providing the light beam 130 and triangular wall portions 142 and 144 having formed integrally and generally intermediately thereof reflecting prisms 148 and 150, respectively. It will be further understood that improved cuvette 100 passes the light beam 130 from a suitable source thereof, such as photoemitter 132, through the cuvette and the medium with test reagent system received within the cavity 122 by total internal reflectance with the internal reflectance occurring, as in embodiment 10 of FIG. 5, at the interface between the cuvette closed wall 118 and the surrounding air due to the respective densities of the medium, wall 118 and the surrounding air; thus, the light beam 130 strikes wall air interface above the critical angle $\theta_1$ for total internal reflectance, is reflected internally therefrom and strikes the interface again at an angle $\theta_2$ above the critical angle whereafter the light beam is reflected, as indicated by arrow 134, back along a line generally parallel to and in the opposite direction to the direction of the line of entry of the light beam 130 into the cuvette and medium whereafter the light beam is received by the photodetector 136.

Improved cuvette 200, FIG. 15, functions similarly to improved cuvette 10A of FIG. 6, i.e. the material of which the optically transparent cuvette 200 is made is less dense than the medium received within the cavity 222 and thus the light beam passes through the cuvette 200 and the above-described optically transparent medium with test reagent system received within the cavity 222 by total internal reflectance, as indicated by arrows 230, 233 and 234, but with the internal reflectance occurring at the interface between the medium received within the cavity 222 and angular surfaces 161 and 162 of the closed wall 218 as shown; angular surfaces 161 and 162 are disposed generally at 45° with respect to the analytical light beam and it will be understood that angles $\theta_1$ and $\theta_2$ are above the critical angle $\theta_c$ for total reflectance. Closed wall 218 is generally rectangularly shaped and extends upwardly from a generally rectangularly shaped base and includes four wall portions 241, 242, 243 and 244 which cooperate with the base to provide cavity 222 which is generally rectangularly shaped in plan; wall 241 is for being disposed generally perpendicular to the photoemitter 232 and the photodetector 236.

In the alternative embodiment illustrated in FIG. 16, improved cuvette 300 causes the light beam 330 to pass therethrough and through the medium including a test reagent system received within the cavity 322 by total internal reflectance. Cuvette 300 includes a bottom generally rectangularly-shaped in plan including a base and a closed wall 318 generally rectangularly-shaped in plan extending upwardly from the base. Wall 318 includes four wall portions, 341, 342, 343 and 344 with the wall 341 being provided with a convex lens 346 formed integrally and intermediately thereof as shown. Wall 342 includes an internal surface 347 which may be provided with a suitable mirror 348 suitably secured thereto and disposed generally centrally thereof; alternatively, at least the central portion of the internal surface 347 of wall portion 342 may be suitably mirrored in the manner known to those skilled in the art. Wall portion 341 is for being disposed generally perpendicular to a photoemitter 332 and photodetector 336 as illustrated in FIG. 16. The analytical light beam 330 emanating from the photoemitter 332 passes through the convex lens 346 and is directed to the mirror 348 passing through the medium including the test reagent system received within the cavity 332 whereupon the light beam is reflected as illustrated passing again through the convex lens 346 and being directed as illustrated by arrow 334 to the photodetector 336.

It will be further understood that the alternative improved cuvette embodiments 100, 200, and 300 of FIGS. 14, 15 and 16 may be provided with the lancet 12 as shown or may not be provided with the lancet 12 in accordance with the teachings of the present invention.

It will be expressly understood that the present invention embodies both the described and shown cuvettes in combination with a lancet as well as without the lancet and that patent protection is sought for the cuvette both with and without the lancet.

Referring now to FIGS. 17-23, there is illustrated an alternate embodiment of combination cuvette and lancet embodying the present invention and identified generally by numerical designation 410; the cuvette is indicated by general numerical designation 420 and a lancet support member is indicated by general numerical designation 460.

Figure 20:
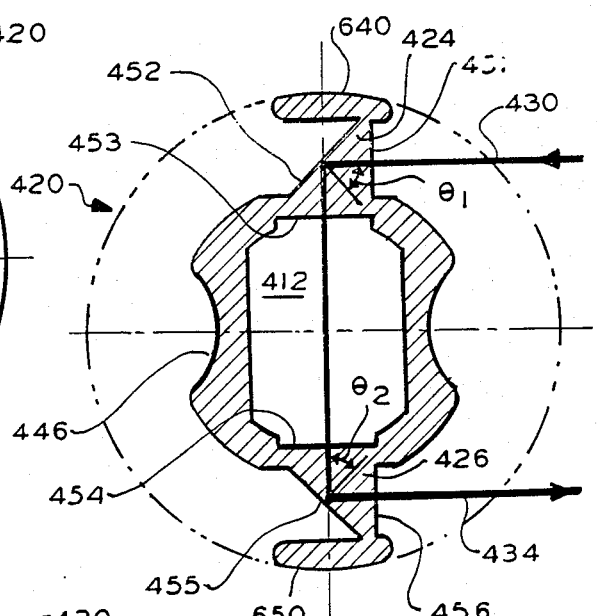
FIG. 20 is a cross-sectional view taken generally along the line 20—20 in FIG. 18 in the direction of the arrows.
Figure 18:
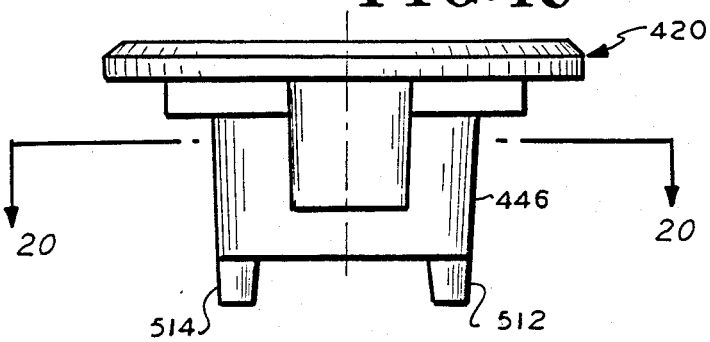
FIG. 18 is a side elevational view of the cuvette shown in FIG. 17.

Before presenting a detailed description of the structure and function of combination cuvette and lancet 410, a general teaching of the structure and function of this alternative embodiment will be presented for convenience of understanding. Cuvette 420 (FIGS. 19, 20 and 22) provides a cavity 412 for receiving an optically transparent gel body provided with a reagent test system of the type taught above and is provided with integrally formed optical elements indicated by general numerical designations 424 and 426, which may be reflecting prisms such as reflecting prisms 48 and 50 illustrated in FIGS. 5 and 8 and described above, and further with a shape for eliminating refractance whereby a beam of light 430, as illustrated in FIG. 20 (and similar to the teachings illustrated in FIGS. 5, 6, 14 and 15) is caused to pass through the cuvette 420 and through the optically transparent medium contained in the cavity 412 by total internal reflectance and for causing the beam of light reflected back along the line indicated by arrow 434 (FIG. 20) generally parallel to the direction of entry of the beam of light 430 into the cuvette and in the opposite direction to the direction of entry of the beam of light into the cuvette. This structure and function, as taught above, has been found to be particularly useful with an OPTICAL ANALYZER of the type illustrated in U.S. patent application Ser. No. 888,754 identified above. Further, it will be understood generally, and for further utility with such OPTICAL ANALYZER, as in the earlier embodiment described above and illustrated in FIGS. 9-13, the lancet support member 460 is provided for supporting a lancet, e.g. lancet 462 (FIGS. 22 and 23) for being advanced into engagement with the skin of a person to puncture the skin and produce the body fluid of interest, e.g. a droplet of blood. In this embodiment, unlike the earlier embodiment, the lancet 462 is mounted not for advancement with the combination cuvette and lancet 410 but instead is mounted for independent advancement with respect to the cuvette whereby the cuvette and optically transparent medium contained therein may be maintained stationary and in constant optical alignment with optical analyzing structure, such as for example that included in the above-noted OPTICAL ANALYZER, at all times. Further, it will be understood generally that the cuvette 420 of this embodiment, unlike the earlier embodiments, is structured so as to be filled not from the top but rather from the bottom and to this end the cuvette 420 is provided with a sealing cap indicated by general numerical designation 428 (FIG. 22) for sealing the top of the cuvette cavity 412 during filling. The bottom of the cuvette cavity 412, as will be taught in detail below, is closed by a top portion of the lancet support member 460, but before the lancet support member is secured to the bottom of the cuvette 420, the sealing cap 428 seals the top of the cuvette cavity 412, the cuvette 420 is inverted, and the cavity 412 is filled with the optically transparent medium such as the above-noted optically transparent gel body provided with a reagent test system. It has been found, preferably, that by filling the cuvette cavity 412 from the bottom, and with the top sealed, overflow problems are prevented during filling of the cuvette cavity 412 with the optically transparent gel body which at the time of filling is in a liquid, or substantially liquid in a state, and in addition, since the bottom portion of the sealing cap 428 is provided with a plug member 429 (FIG. 22) which cooperatively provides, in combination with the top portion 437 of the cuvette 420, a uniform or even top surface to the cuvette cavity 412 which in turn provides a flat or uniform top surface to the optically transparent medium or gel body upon filling the inverted cavity 412 and particularly after hardening; such flat or uniform top gel body surface has been found to enhance the diffusion characteristic of the gel body. After such filling, the lancet support member 460 is secured to the bottom of the cuvette 420 to close the cuvette cavity 412 whereafter the filled cuvette 420 is re-inverted for subsequent use.

Referring now to specific structure and function, cuvette 420 (FIG. 22) includes a body member indicated by generaly numerical designation 440 in turn including a generally funnel-shaped or inverted conically shaped upper portion 442 including the above-noted bottom 437, an inwardly extending generally spherical surface 443 and a closed wall or closed wall portion 446 (particularly FIGS. 18–21) formed integrally with the upper portion 442 and extending downwardly therefrom. The closed wall 446 includes opposed angular wall portions indicated by general numerical designations 447 and 448 (FIG. 22) providing, respectively, the above-noted optical elements 424 and 426 which, of course, are in turn fomred integrally with the closed wall 446.

Optical element 424 (FIG. 19, 20 and 22) may be provided with a flat outer surface 451 for being disposed perpendicular to a beam of light 430 (FIG. 20), an outer angular surface 452 disposed at an angle with respect to the outer flat surface 451 to cause the beam of light 430 to internally strike the interface between the angular surface 452 and the surrounding medium (e.g. air) at an angle $\theta_1$ (FIG. 20) above the critical angle $\theta_c$ for total internal reflectance as taught above, and an inner flat surface 453 for being disposed perpendicular to the beam of light. Similarly, optical element 426 is provided with an inner flat surface 454 for being disposed perpendicular to the beam of light, and outer angular surface 455 disposed at an angle $\theta_2$ (FIG. 20) with respect to the inner flat surface 454 to cause the beam of light 430 to internally strike the interface between the angular surface 455 and the surrounding medium (e.g. air) above the critical angle $\theta_c$ for total internal reflectance, and a flat outer surface 456 for being disposed perpendicular to the beam of light, e.g. arrow 434 pf FIG. 20 upon exiting the cuvette 420. It will be understood, with regard to FIG. 20, that the beam of light 430 may be provided by a suitable source such as the photoemitter 32 of FIG. 5, and may be received upon exiting the cuvette 420 by a suitable optical receiver such as the photodetector 36 of FIG. 5.

The lancet support member 460, FIG. 22, it will be generally understood, is for being secured to the bottom of the cuvette 420 to close the cavity 412 as noted above and for performing its function described below and includes a top member 470 and a bottom member 480. The bottom member 480 of the lancet support member 460 includes a resilient rearward portion 482 and a forward portion 484. The top member 470 of the lancet support member 460 includes a rearward portion 472 and a forward portion 474 with the top and bottom members 470 and 480 being secured together, such as for example, by upwardly extending tapered post 486 provided on the bottom member 480 which tapered post is received in interference fit with an inwardly extending tapered hole 476 formed in the upper member 470. It will be understood, although not shown, that the top member 470 is provided with a downwardly extending tapered post, not shown, received in interference fit within tapered hole 487 provided in the bottom member 480. The forward portions 474 and 484 of the top and bottom members 470 and 480 provide, cooperatively, an internal chamber 488 for slidably receiving the lancet 462 with the forward tip 468 of the lancet for being extended outwardly through a surrounding opening indicated by general numerical designation 464 formed cooperatively by inwardly curved surfaces 479 and 489 formed respectively in the top and bottom members 470 and 480 of the lancet support member 460. As best may be seen by referring to the bottom member 480 of the lancet support member 460 as shown at the lower portion of FIG. 22, the rearward portion 465 of the lancet 462 is secured to resilient rearward portion 482 of the lower member 480 of the lancet support member 460, for movement therewith, by being received within an opening or slot shown in cross-section and indicated by numerical designation 481. For alignment maintenance, the lancet 462 may be provided with a guide member 467, for example molded integrally therewith, and provided with a shape complementary to the shape of the chamber 488. Further, for further alignment maintenance, the lower member 480 may be provided with an inwardly curved slot or groove 483.

For sterility and safety prior to use of the lancet 462 to produce skin puncture and produce a body fluid of interest, the tip 468 of the lancet 462 may be provided with an integrally formed, such as by molding, protective member or shroud 490, shown in FIG. 24, and which may be conveniently removed prior to use of the lancet 462 by twisting of the protective member 490 with respect to the lancet.

For assembly, and referring particularly to FIG. 22, the top member 470 and bottom member 480 of the lancet support member 460 will first be assembled by being secured together by the tapered posts and holes 486, 476, 487 described above. Thereafter, the lancet support member 460 is secured to the bottom of the cuvette 420 as generally described above. For such subsequent assembly, it will be noted that the bottom of the closed wall 446 of the cuvette 420 (also note FIG. 19) is provided with a plurality of downwardly extending tapered posts 510, 512, 514 and 516 for being received in interference fit in correspondingly located inwardly extending tapered holes 520, 522, 524 and 526 formed in the top of the rearward portion 472 of the top member 470 of the lancet support member 460. Thereafter, the combination cuvette and lancet 410 may be placed in a suitable analytical device, such as the above-noted OPTICAL ANALYZER, for use.

Referring specifically to the structure of the sealing cap 428, shown at the top portion of FIG. 22, it will be understood that the bottom surface 429 of the sealing cap 428 is complementary in shape to the top surface 443 of the upper funnel-shaped portion 442 of the cuvette 420 and that the plug member 429 of the sealing cap is complementary in shape to the tapered hole 421 formed centrally of the bottom 437 of the funnel-shaped portion 442 of the cuvette 420; sealing cap plug 429 and opening 421 are provided with a suitable interference fit.

To place the body fluid of interest in the cavity 412 of the cuvette and, for example, diffusion of the body fluid of interest into the optically transparent gel body contained in the cavity 412, the sealing cap 428 will be removed, suitable force (such as from a member connected to a compression spring such as compression spring 40 shown in FIG. 2 of the above-noted U.S. patent application Ser. No. 888,754 entitled OPTICAL ANALYZER) indicated by arrow 550 in FIG. 23 will be applied to the resilient rearward portion 482 of the lower member 480 of the lancet support member 460, to advance or flex the resilient rearward portion 482, as shown in FIG. 23, inwardly or forwardly to in turn advance the lancet 462 forwardly and slidably within the chamber 488 of the lower member 480 to cause the lancet tip 468 to puncture the skin of a person, for example of the finger of a person, to produce a body fluid of interest, namely a droplet of blood. The person may thereafter wipe the droplet of blood across the inwardly extending surface 443 of the upper funnel-shaped portion 442 of the cuvette 420, such surface serving as a depression which facilitates wiping of the droplet of blood across the opening 421 and entry of the droplet of blood into and through the opening 421 into the cavity 412 for diffusion into the optically transparent gel body contained therein. Thereafter, as noted above, the optically transparent medium, e.g. gel body, contained in the cavity 420 undergoes a change in at least one optical transmissive property which modifies the beam of light passing through the gel body thereby permitting the body fluid of interest, e.g. blood, to be analyzed as noted above.

Referring again to FIG. 23, after the force 550 has been removed, it will be understood that the resilient rearward portion 482 of the lower member 480 of the lancet support member 460 will flex outwardly and return to its original shape shown in the lower portion of FIG. 22 thereby retracting the lancet 482 inwardly sufficiently far such that the lancet tip 468 reside inwardly of the forward portions 474 and 484 of the top and bottom members of the lancet support member 460 for safety.

In general summary, it will be understood that the combination cuvette and lancet 410 of the alternate embodiment shown in FIGS. 17–22 functions substantially the same as the embodiment shown in FIGS. 9–13 and described above with the beam of light 430, FIG. 20, being caused to pass through the cuvette 420, and optically transparent gel contained in the cavity 412, by total internal reflectance, as described in detail above, and to cause the beam of light to be reflected back along a line generally parallel to the direction of the line of entry of the beam of light into the cuvette and in the opposite direction of the entry of the beam of light in the cuvette, as illustrated by arrows 430 and 434 of FIG. 20.

It will be further understood by those skilled in the art that the cuvette 420, FIGS. 17–22, is useful both with and without the lancet and lancet support member 460 and such is within the contemplation of the present invention. In this regard, referring to FIG. 25, instead of closing the bottom of the cavity 412 of the cuvette 420 with the top of the combination lancet and support member 460, alternatively a cavity closure member indicated by general numerical designation 600 may be provided to close the bottom of the cavity 412. As may be noted in FIG. 25, the top portion of the cavity closure member 600 may be provided with a plurality of inwardly extending openings 610, 612, 614 and 616 which are tapered to receive in interference fit with the downwardly extending tapered posts 510, 512, 514 and 516 provided on the closed wall 446 of the cuvette 420. Further, the top of the cavity closure member 600 may be provided with upwardly extending plug portion 620 complementary in shape to the bottom of the cavity 412, and for being received therein.

Figure 19:
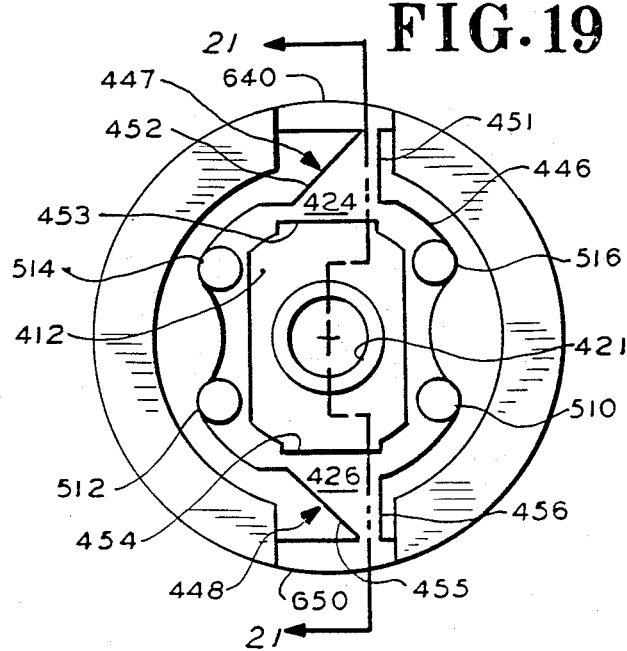
FIG. 19 is a bottom view of the cuvette of FIGS. 17 and 18.
Figure 21:
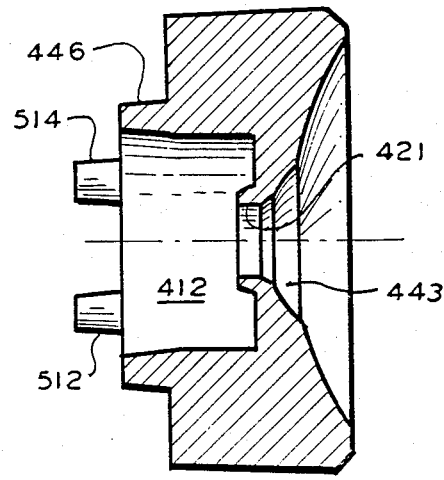
FIG. 21 is a cross-sectional view taken generally along the line 21—21 in FIG. 19 in the direction of the arrows.

Referring again to the upper portion of FIG. 22 and FIGS. 19 and 20, it will be noted that the cuvette 420 may be provided with integrally formed, such as by molding, finger guard members 640 and 650. Finger guard members 640 and 650 are particularly useful to facilitate handling of the cuvette 420 by an operator and are particularly useful for preventing engagement of the handling operator's fingers with the outer surfaces 451 and 452 of optical element 424 and outer surfaces 455 and 456 of optical element 426 thereby preventing smearing or smudging of these outer optical surfaces with fingerprints from the handling operator and the placement of body oil, dirt, etc. from the fingers of the handling operator on these outer surfaces of the optical elements.

It further will be understood by those skilled in the art that many modifications and variations may be made in the present invention without departing from the spirit and the scope thereof.

What is claimed is:

1. A combination lancet and cuvette apparatus, comprising:

cuvette providing a cavity for receiving an optically transparent medium including a reagent test system for reacting with a sample portion of a fluid of interest; said cuvette made of optically transparent material and provided with a shape and optical elements for causing a beam of light to pass therethrough and through said medium by total internal reflectance and for causing said beam of light to be reflected back along a line different from the direction of the line of entry of said light beam into said cuvette;

a lancet provided on and extending from said cuvette and including a rearward portion and a forward tip for producing skin puncture to produce said body fluid of interest;

said cuvette comprising a cuvette body member including a generally funnel-shaped upper portion including a bottom and an inwardly extending generally spherical surface providing a depression, and a closed wall portion formed integrally with said upper portion and extending downwardly therefrom, said closed wall including opposed wall portions provided with integrally formed opposed angular portions providing said optical elements with each optical element including flat outer and inner surfaces for being disposed perpendicular to said beam of light and an outer angular surface for being disposed at a predetermined angle with respect to one of said flat surfaces;

said lancet comprising a lancet support member including a resilient rearward portion and a forward portion, said rearward and forward portions of said lancet support member cooperatively providing an internal chamber for slidably receiving said lancet with said forward tip of said lancet extending outwardly out of said lancet support member through an opening formed in said forward portion of said lancet support member and with said rearward portion of said lancet secured to said resilient rearward portion of said lancet support member, upon sufficient force being applied externally to said resilient rearward portion of said lancet support member said resilient rearward portion being bowed inwardly to advance said lancet sufficiently forward to cause said forward tip of said lancet to produce said skin puncture and provide said body fluid of interest;

said closed wall including a bottom portion and said rearward portion of said lancet support member including a top portion, said bottom and top portions provided with mutually engageable connecting members for securing said lancet support member to the bottom portion of said closed wall and upon said top portion of said rearward portion of said lancet support member being secured to said bottom portion of said closed wall, said top portion of said rearward portion of said lancet support member, said closed wall and said bottom of said generally funnel-shaped upper portion providing in combination said cavity for receiving said medium including a reagent test system;

said bottom of said generally funnel-shaped upper portion provided with a centrally formed access opening extending therethrough and providing access to said cavity for said sample portion and said depression for facilitating wiping of said sample portion of said fluid of interest into and through said access opening and into said cavity; and upon said beam of light perpendicularly striking said outer flat surface of one of said angular portions of said closed wall, said beam of light entering and passing into said one angular portion substantially without refractance and striking the interface between said outer angular surface of said one angular portion and the surrounding medium at an angle above the critical angle for total internal reflectance and being reflected internally therefrom through said one angular portion and exiting said flat inner surface of said one angular portion substantially without refractance, said beam of light continuing through said cavity, through said optically transparent medium and perpendicularly striking said flat outer surface of said other angular portion and passing into said other angular portion substantially without refraction and striking the interface between said outer angular surface of said other angular portion and the surrounding medium at an angle above the critical angle for total internal reflectance and being reflected internally therefrom through said other angular portion and perpendicularly exiting said outer flat surface of said other angular portion substantially without refractance.

2. Apparatus according to claim 1 wherein said mutually engageable connecting members comprise a plurality of outwardly extending tapered posts provided on one of said bottom portion of said closed wall and top portion of said rearward member and a plurality of inwardly extending tapered holes for receiving said posts in interference fit provided on the other of said bottom portion of said closed wall and said top portion of said rearward portion of said lancet support member.

3. Apparatus according to claim 1 wherein said apparatus further includes a protective member molded integrally on the forward tip of said lancet, said protective member for being removed by being twisted relative to said forward tip of said lancet prior to said skin puncture.

4. Cuvette apparatus, comprising
cuvette providing a cavity for receiving an optically transparent medium including a reagent test system for reacting with a sample portion of a fluid of interest; said cuvette made of optically transparent material and provided with a shape and optical elements for causing a beam of light to pass therethrough and through said medium by total internal reflectance and for causing said beam of light to be reflected back along a line different from the direction of the line of entry of said light beam into said cuvette;

said cuvette comprising a cuvette body member including a generally funnel-shaped upper portion including a bottom and an inwardly extending generally spherical surface providing a depression, and a closed wall portion formed integrally with said upper portion and extending downwardly therefrom, said closed wall including opposed wall portions provided with integrally formed opposed angular portions providing said optical elements with each optical element including flat outer and inner surfaces for being disposed perpendicular to said beam of light and an outer angular surface for being disposed at a predetermined angle with respect to one of said flat surfaces;

bottom means providing a bottom of said closed wall and said bottom means, said closed wall and said bottom of said generally funnel-shaped upper portion providing in combination said cavity for receiving said medium including a reagent test system;

said bottom of said generally funnel-shaped upper portion provided with a centrally formed access opening extending therethrough and providing access to said cavity for said sample portion and said depression for facilitating wiping of said sample portion of said fluid of interest into and through said access opening and into said cavity; and upon said beam of light perpendicularly striking said outer flat surface of one of said angular portions of said closed wall, said beam of light entering and passing into said one angular portion substantially without refractance and striking the interface between said outer angular surface of said one angular portion and the surrounding medium at an angle above the critical angle for total internal reflectance and being reflected internally therefrom through said one angular portion and perpendicularly exiting said flat inner surface of said one angular portion substantially without refractance, said beam of light continuing through said cavity and said optically transparent medium and perpendicularly striking said flat inner surface of said other angular portion and passing into said other angular portion substantially without refraction and striking the interface between said outer angular surface of said other angular portion and the surrounding medium at an angle above the critical angle for total internal reflectance and being reflected internally therefrom through said other angular portion and perpendicularly exiting said outer flat surface of said other angular portion substantially without refractance.

5. Apparatus according to claim 1 or 4 wherein said apparatus further includes a sealing cap including a bottom surface substantially complementary in shape to said top surface of said generally funnel-shaped upper portion of said cuvette and including a centrally formed, downwardly extending plug member complementary in shape to said access opening formed in the bottom of said generally funnel-shaped upper portion and for being received in an interference fit with said access opening to seal said cavity.

* * * * *